United States Patent [19]

Hoki

[11] Patent Number: 5,046,113
[45] Date of Patent: Sep. 3, 1991

[54] METHOD OF AND APPARATUS FOR DETECTING PATTERN DEFECTS BY MEANS OF A PLURALITY OF INSPECTING UNITS EACH OPERATING IN ACCORDANCE WITH A RESPECTIVE INSPECTING PRINCIPLE

[75] Inventor: Tetsuo Hoki, Kyoto, Japan

[73] Assignee: Dainippon Screen Mfg. Co. Ltd, Japan

[21] Appl. No.: 296,435

[22] Filed: Jan. 12, 1989

[30] Foreign Application Priority Data

Jan. 12, 1988 [JP] Japan .................... 63-3960

[51] Int. Cl.[5] .............................................. G06K 9/00
[52] U.S. Cl. .......................................... 382/8; 382/48; 358/106
[58] Field of Search .......................... 382/8, 41, 48, 49; 358/101, 106, 107

[56] References Cited

U.S. PATENT DOCUMENTS

| | | | |
|---|---|---|---|
| 4,441,207 | 4/1984 | Lougheed et al. | 382/8 |
| 4,589,140 | 5/1986 | Bishop et al. | 382/8 |
| 4,651,341 | 3/1987 | Nakashima et al. | 382/8 |
| 4,692,943 | 9/1987 | Pietzsch et al. | 358/107 |
| 4,870,693 | 9/1989 | Arai et al. | 382/61 |

Primary Examiner—David K. Moore
Assistant Examiner—Jose L. Couso
Attorney, Agent, or Firm—Ostrolenk, Faber, Gerb & Soffen

[57] ABSTRACT

An apparatus for inspecting pattern defects in circuit board conductors or other images has inspecting units which perform inspection operations based on various pattern matching approaches, which include design rule checking and expansion/contraction processing. Each of the inspecting units inspects a part of the pattern of an object. The part of a pattern is defined by a respective inspection and inhibition domain defining signals. The domain signals are formed with the aid of a scanning device and a binarizing circuit, a CAD system and a converter, a digitizer and a converter and the like. The apparatus then displays inspection decisions derived from each inspecting unit on a display unit, with respect to the different domains.

19 Claims, 13 Drawing Sheets

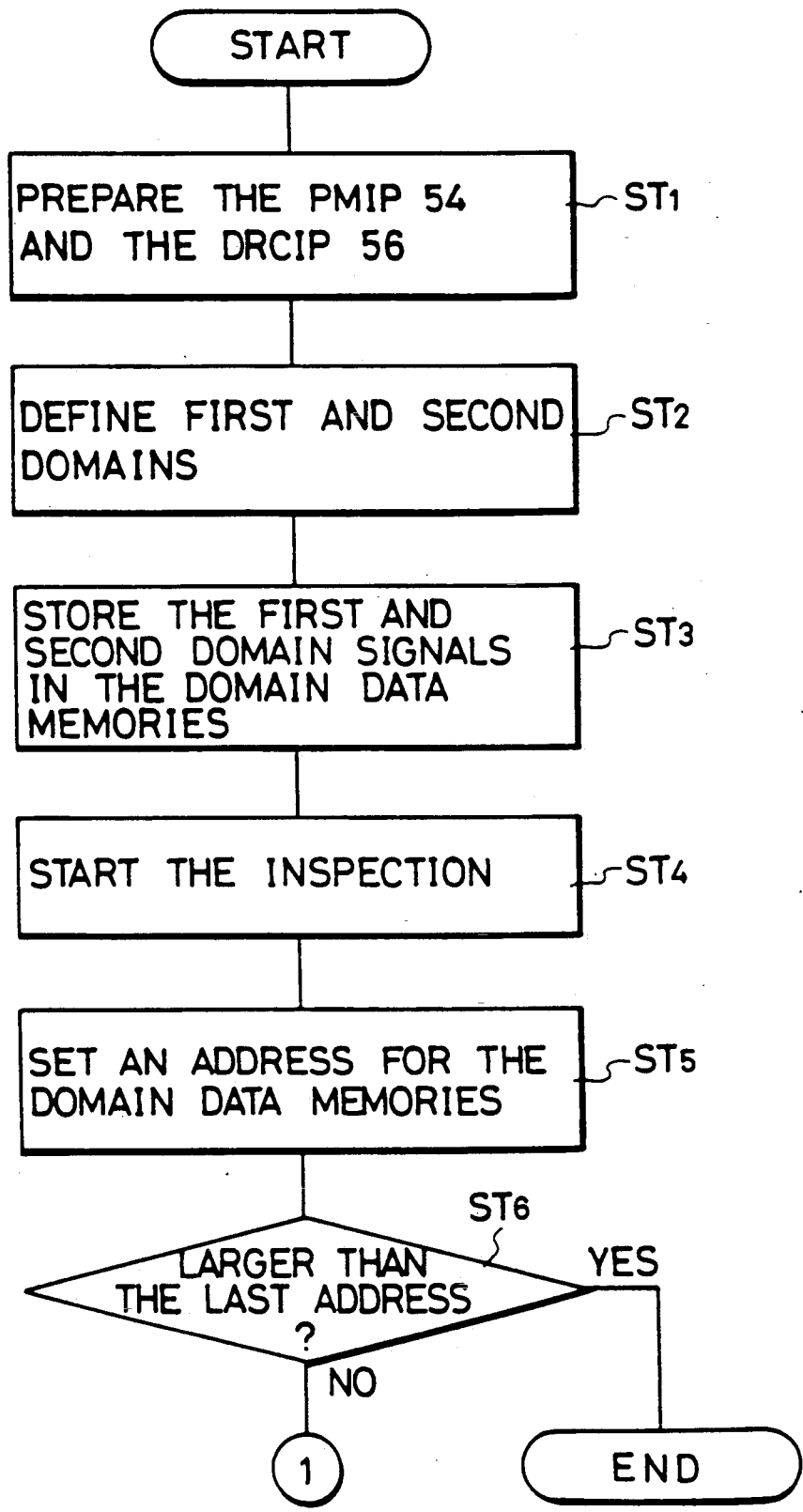

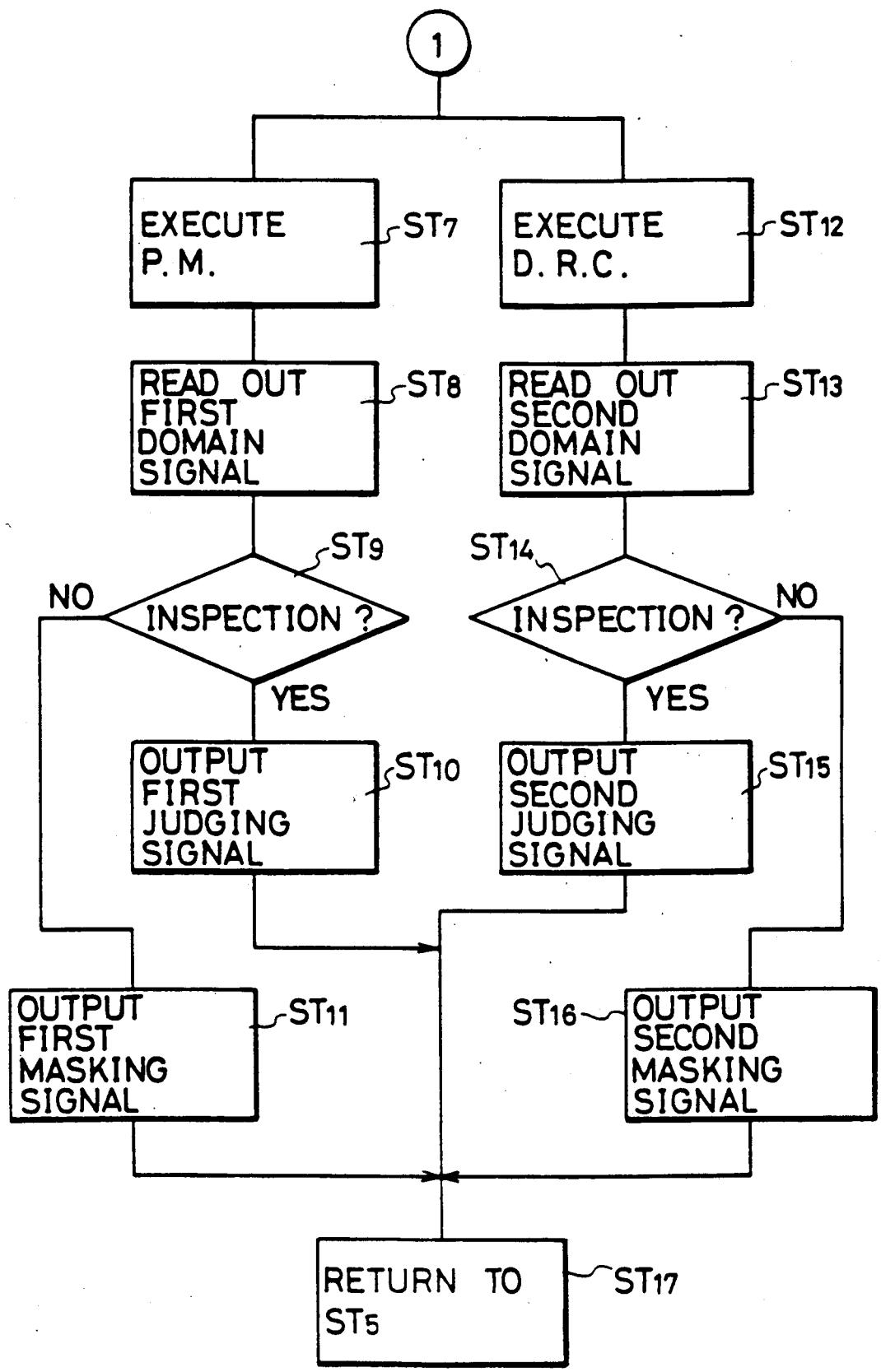

Fig.11
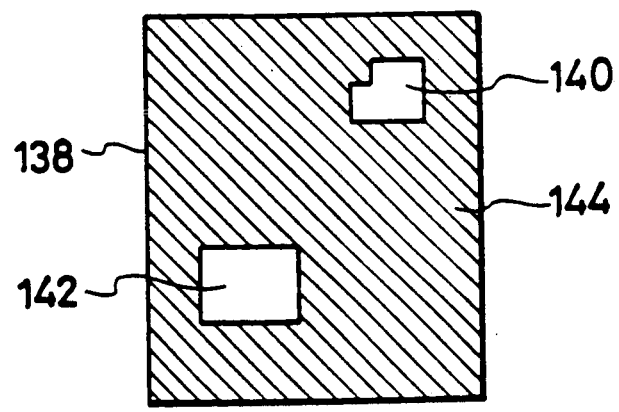
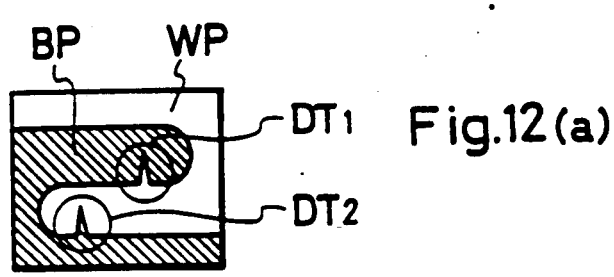
Fig.12(a)
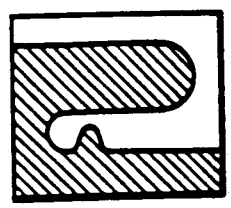
Fig.12(b)
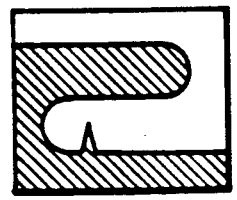
Fig.12(c)
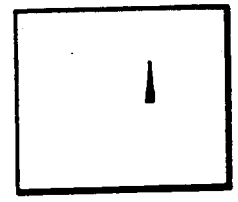
Fig.12(d)
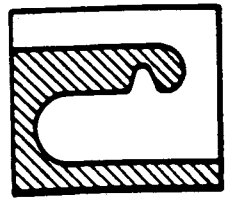
Fig.12(e)
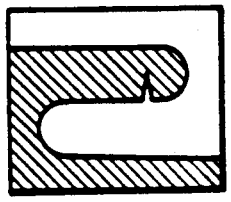
Fig.12(f)
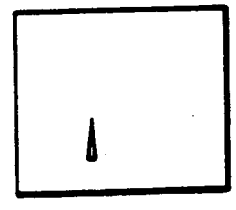
Fig.12(g)

METHOD OF AND APPARATUS FOR DETECTING PATTERN DEFECTS BY MEANS OF A PLURALITY OF INSPECTING UNITS EACH OPERATING IN ACCORDANCE WITH A RESPECTIVE INSPECTING PRINCIPLE

BACKGROUND OF THE INVENTION

The present invention relates to a method and apparatus for detecting pattern defects in products such as printed writing boards, IC mask patterns, lead frames and the like.

In pattern defect detection, there are many kinds of defects to detect as, for example, a mouse bite, a bump, a disconnection, a widening, a narrowing, a bridging, a pin holing and remaining copper. These defects are illustrated in FIG. 15 by a mouse bite portion 2, a bump portion 4, a copper disconnection 6, a wide copper portion 8, a narrow copper portion 10, a bridge portion 12, a pin hole portion 14 and a remaining copper portion 16. Detecting such pattern defects on printed wiring boards and the like is mainly carried out in the prior art by a pattern matching method and by a design rule check method.

In the conventional "pattern matching" method, an image pattern of a reference object is overlapped and compared to an image pattern of an object to be inspected, and then the pattern defects are evaluated by detecting discrepancies in image patterns between the reference object and the object being inspected. This method is described, for example, in Japanese Patent Kokoku Publication No. 2069/1984, Japanese Patent Kokai Publication No. 61604/1985 and Japanese Patent Kokai Publication No. 140009/1987.

In the known "design rule check" method, various features of a reference image pattern, such as line width, angle, specific pattern, defective form and the like, are stored and compared with the features of an image pattern to be inspected, and then the pattern defects are evaluated by detecting image patterns which are different from all of the reference features, or by noting forms which are known to be defective. This method is, for example, known from Japanese Patent Kokai Publication No. 167649/1982 and Japanese Patent Kokai Publication No. 149905/1982.

The aforementioned methods have respective merits and disadvantages in their pattern defects detecting ability. For example, the pattern matching method can detect the pattern defects without limitation as to form. In a case where image patterns are read in high resolution, however, it is possible to detect image discrepancies which are not real pattern defects but which are caused by quantization errors, arising from quantization procedures and forming errors, others which arise during forming of image patterns on the objects, which cause harmless deviations, between the reference object and the objects being fabricated.

In the design rule check method, it is possible to detect the pattern defects without the reference image pattern which is essential to the pattern matching method, and it has superior ability for detecting fine pattern defects. However, in a case of inspecting a character, a special figure as shown in FIG. 16 and a power supply line on a multi-layer print wired board applicable to high density wiring, it is likely for a scrap portion 18, projections portions 20 and 22, a disconnection portion 24 and an undersized portion 26 to be adjudged as a pattern defect by the error recognition procedure even though they are not real pattern defects.

Although detection of the pattern defects was carried out by either the pattern matching method and the design rule check method, the detecting method was not always applicable to the image patterns in the prior art since each method had its aforementioned peculiar disadvantages. Therefore, productivity and yield in the prior art methods for testing suffered, in part due to its consideration of information which was not relevant to the pattern inspection of the object.

SUMMARY OF THE INVENTION

Accordingly, the present invention has been developed with a view of substantially eliminating the above described disadvantages inherent in the prior art and has as its essential object to provide an improved method and apparatus for detecting pattern defects.

The object is accomplished by the present invention, in accordance with a first aspect thereof by a method of inspecting pattern defects of an object to be inspected comprising the steps of (a) preparing a plurality of inspecting units for the object, each said inspecting unit having a proper inspecting principle, (b) storing groups of domain signals in a memory device corresponding to addresses of the object, each said group of domain signals comprising inspection signals and inhibition signals, each said group of domain signals also having a relation with the respective prepared inspecting unit, (c) scanning and binarizing an image of the object, (d) reading out the domain signals of every group stored in the memory device according to an address of an inspecting position on the object, (e) controlling the operation of each inspecting unit according to each kind of the respective domain signal read out from the memory device at the step (d), and (f) forming an inspection decision according to an output signal of the inspecting units.

It is preferable that the step (b) further comprises the steps of (b-1) defining an inspection domain corresponding to the inspection signals and an inhibition domain corresponding to the inhibition signals on defining means, said domains being defined for each inspecting unit, (b-2) obtaining groups of binary signals by scanning and binarizing each image of defining means, and (b-3) storing the groups of binary signals in the memory device corresponding to addresses of the defining means.

Practically, it is preferable that the defining means is a film painted at one or the other or both the inspection domain and the inhibition domain.

It is also preferable that the defining means is a plate which has a punched hole forming either the inspection domain or the inhibition domain.

Moreover, it is preferable that the groups of domain signals are stored in the memory device by receiving groups of binary signals, each said group of binary signals forming an inspection domain and an inhibition domain.

Practically, it is preferable that the group of the binary signals is obtained by converting CAD data created with a CAD system into the binary signals.

It is also preferable that the group of the binary signals is obtained by converting digitized signals generated with a digitizer into the binary signals.

Further, it is preferable that the operation of the inspecting unit is inhibited when the memory device reads out the inhibition signal corresponding to the inspecting unit.

Practically, it is preferable that an output signal of the inspecting unit is nullified with gate means according to reading of the inhibition signal from the memory means.

It is also preferable that an input signal of the inspecting unit is nullified with gate means according to reading of the inhibition signal from the memory means.

In the second aspect of the invention, an apparatus for inspecting pattern defects of an object to be inspected comprises binary signal generating means for generating binary signals by reading and binarizing an image pattern, a plurality of inspecting units for inspecting the pattern defects by using the binary signals of the object, each said inspecting unit having a proper inspecting principle, defining means for defining an image pattern forming an inspection domain and an inhibition domain, a memory device for storing groups of binary signals of the defining means, selecting means for selecting either of the inspecting units and the memory device to receive the binary signals generated by the binary signal generator, an access controller for controlling the operations of reading and writing the binary signals for the memory device according to a reading position of the image patterns, an inspecting controller for controlling the operation of each inspecting unit in response to the binary signals read out from the memory device, and informing means for informing an inspective judgement in response to an output signals of the inspecting units.

It is preferable that the memory device comprises memory devices corresponding to each inspecting unit one by one, the selecting means has a terminal associated with every inspecting unit and terminals associated with each memory device one by one, thereby to receive the binary signals with every inspecting unit or one of the memory devices by selecting one of the terminals.

Moreover, it is preferable that the inspecting controller inhibits the operation of the inspecting unit in response to reading out the binary signal being a predetermined state.

Practically, it is preferable that the operation of the inspecting unit is inhibited by nullifying an output signal of the inspecting unit with gate means.

It is also preferable that the operation of the inspecting unit is inhibited by nullifying an input signal of the inspecting unit with gate means.

In the third aspect of the invention, an apparatus for inspecting pattern defects of an object to be inspected comprises image signal generating means for generating image signals of the object by scanning the same, a plurality of inspecting units for inspecting the pattern defects by using the image signal of the object, each said inspecting unit having a proper inspecting principle, domain signal generating means for generating domain signals, said domain signals comprising inspection signals and inhibition signals, a memory device for storing groups of the domain signals, an access controller for controlling the operations of reading and writing the domain signals for the memory device according to a scanning position of the object, an inspecting controller for controlling the operation of each inspecting unit in response to the domain signals read out from the memory device, and informing means for forming an inspection decision in response to an output signals of the inspecting units.

It is preferable that the domain signal generating means comprises CAD system which creates CAD data forming an inspection domain and an inhibition domain, and converting means for converting the CAD data into the domain signals.

It is also preferable that the domain signal generating means comprises a digitizer which generates digitized signals forming an inspection domain and an inhibition domain, and converting means for converting the digitized signals into the domain signals.

Moreover, it is preferable that the inspecting controller inhibits the operation of the inspecting unit in response to the inhibition signal read out from the memory device.

Practically, it is preferable that the operation of the inspecting unit is inhibited by nullifying an output signal of the inspecting unit with gate means.

It is also preferable that the operation of the inspecting unit is inhibited by nullifying an input signal of the inspecting unit with gate means.

With the aforementioned features, the present invention has the following useful advantage.

The inspecting apparatus can be deployed to produce only that information which is useful for correcting defects. This realizes a greater productivity in producing the products which are being inspected.

The above and other objects, features, aspects and advantages of the present invention will become apparent from the following detailed description of the present invention when taken in conjunction with the accompanying drawings.

BRIEF DESCRIPTION OF THE DRAWINGS

FIGS. 8A and 8B are flow charts showing steps of the pattern defect inspection process in accordance with the first embodiment.

FIG. 11 shows an example of a masking pattern according to an expansion/contraction processing method.

FIGS. 12A-G illustrates a principle of the expansion/contraction process.

Figure 1:
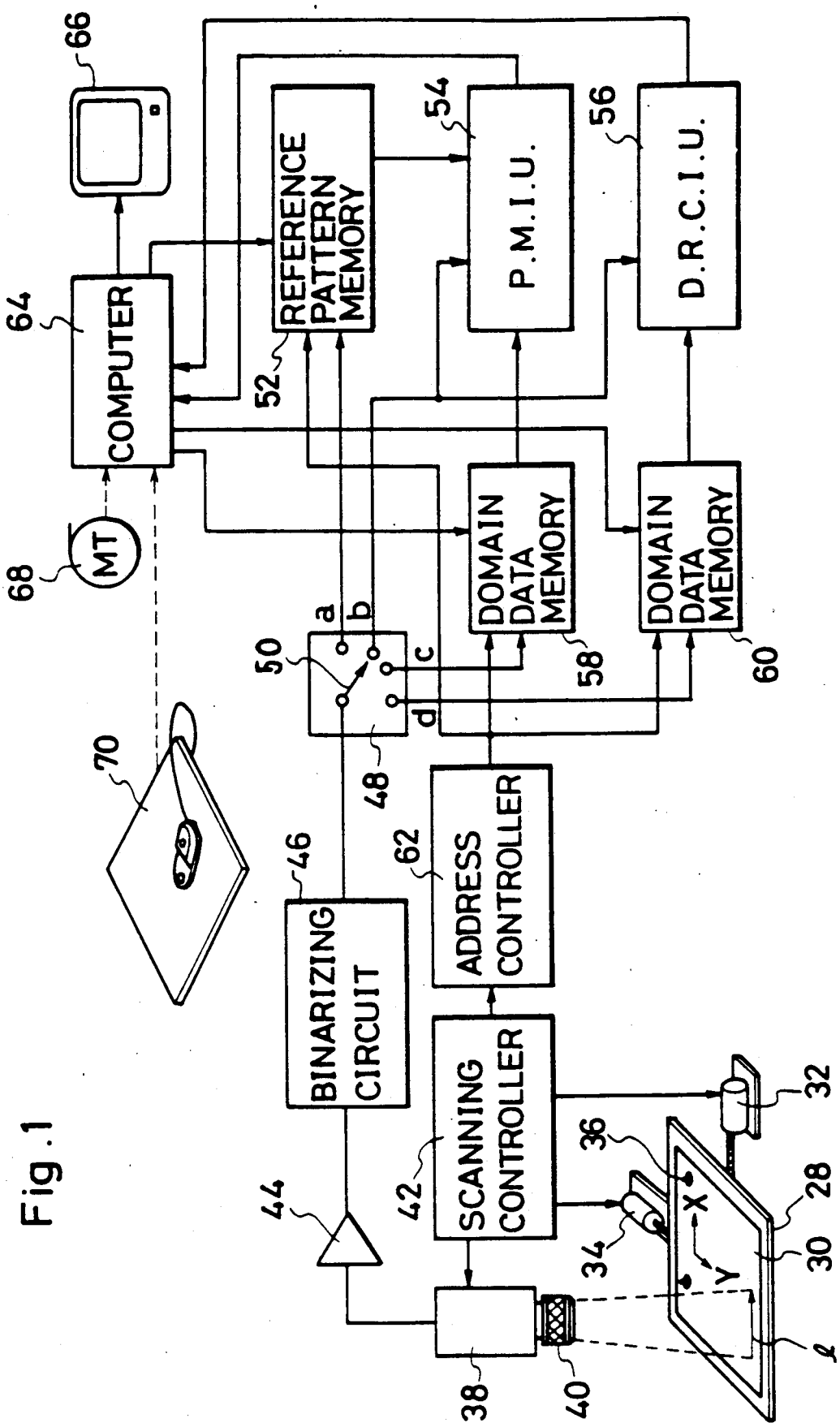
FIG. 1 is a block diagram of a first embodiment of the present invention.

For the purpose of illustrating the invention, there is shown in the drawing several forms which are presently preferred, it being understood, however, that the invention is not limited to the precise arrangements and instrumentalities shown.

DETAILED DESCRIPTION OF THE DRAWINGS

Referring to the drawings, FIG. 1 is a schematic diagram of a pattern defect detecting apparatus. An XY table 28 holding a reference object (not shown) or an object 30 to be inspected such as printed wiring board is driven in an X direction by a motor 32, and in a Y direction by a motor 34. Pins 36 on the XY table 28 hold the objects in place and prevent location errors between the reference object and the object 30.

A line sensor 38 and an optical lens 40 are provided above the XY table 28 at prescribed intervals. The line sensor 38 is generally used with a CCD line sensor having 2048 photoelectric elements forming pixels arrayed in the X direction. The optical lens 40 has a preferred magnification. Then the line sensor 38 and the optical lens 40 read a pattern image on the object 30 with a resolution determined by the magnification of the optical lens 40, and in a scanning width "1" determined by the number of photoelectric elements of the line sensor 38 and the magnification of the optical lens 40.

Figure 2:
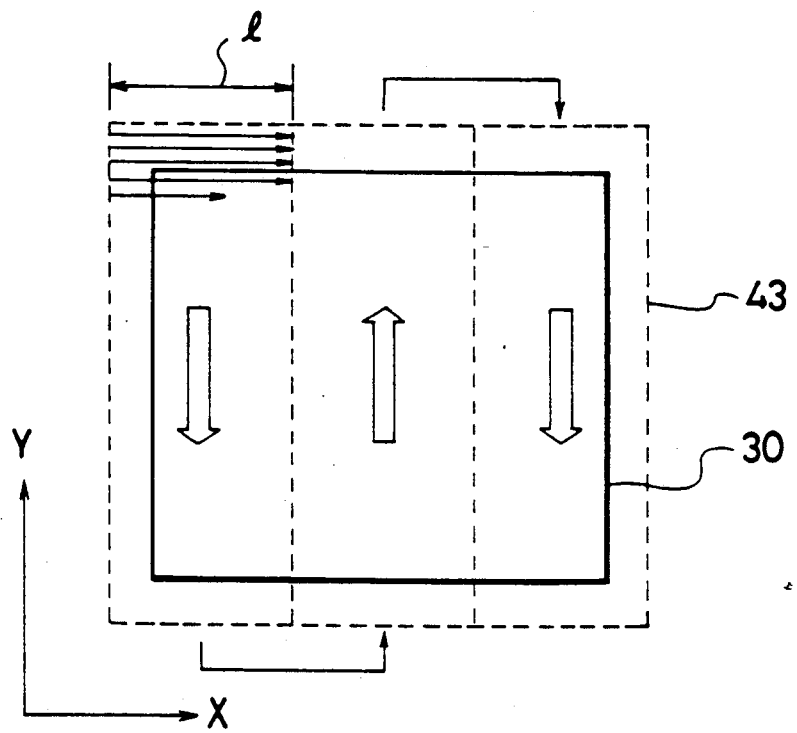
FIG. 2 shows a scanning movement direction for an inspection domain of an image pattern.

In scanning the object 30, a scanning controller 42 supplies two driving signals to respective motors 32 and 34 to enable the line sensor 38 and the optical lens 40 to move relatively to and to thus scan all inspection areas of the object 30. Referring to FIG. 2, the line sensor 38 and the optical lens 40 scan in the X direction while the XY table 28 is moved in the Y direction by the motor 34. Upon completion of a scanning line, the XY table 28 is moved in the X direction by the motor 32 by the scanning width "1", and then the XY table 28 is moved in a contrary Y direction to perform a return scanning. Therefore, the object 30 is scanned over an inspection area 43 with the line sensor 38 and the optical lens 40 by repeating the aforementioned operation. The scanning controller 42 also supplies further driving signals to the line sensor 38 to drive it, and a positional signal corresponding to a scanning position on the XY table 28 to an address controller 62.

An analog image signal read by the line sensor 38 is then amplified by an amplifier 44, and converted by a binarizing circuit 46 into binary signal of "1" and "0", which corresponds to one pixel of the pattern image.

An input selector 48 receives the binary signal generated by the binarizing circuit 46, and delivers it to one of the terminals "a", "b", "c" and "d" according to a selecting input provided to a switching lever 50. The terminal "a" is connected with a reference pattern memory 52 which stores binarized reference pattern signals obtained from the reference object. The terminal "b" is connected with a pattern matching inspection unit (hereinafter referred to as "PMIU") 54 which detects the pattern defects on the object 30 based on the pattern matching method, and a design rule check inspection unit (hereinafter referred to as "DRCIU") 56 which detects the pattern defects on the object 30 based on the design rule check method. The terminal "c" is connected with a domain data memory 58 which stores a group of first domain signals, which represent, for example, the read and binarized version of an image of a masking pattern 80 shown in FIG. 4C, controlling the inspection operation in the PMIU 54. The terminal "d" is further connected with a domain data memory 60 which stores a group of second domain signals, which represent, for example, the read and binarized version of an image of a masking pattern 106 shown in FIG. 7, controlling the inspection operation in the DRCIU 56.

The address controller 62 generates an address signal corresponding to a scanning position on the XY table 28 by converting the positional signal generated by the scanning controller 42 into the address signal. Then the address controller 62 supplies the address signal to the reference pattern memory 52, and to the domain data memories 58 and 60 respectively.

A computer 64 has functions which include controlling read and write operations in each of the reference pattern memory 52, domain data memories 58 and 60, and outputting evaluations of the inspection with the aid of a display unit 66.

Figure 3:
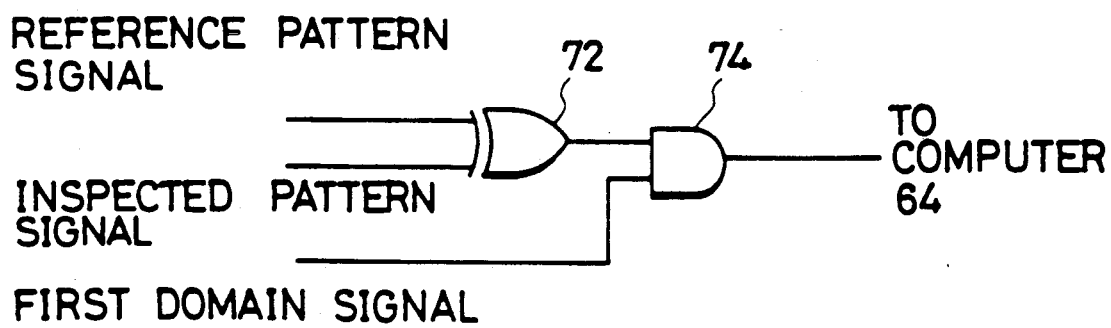
FIG. 3 is a circuit diagram for detecting pattern defects according to the pattern matching method.

Referring to FIG. 3, as shown in the detailed circuit of the PMIU 54, it comprises an EX.OR gate 72 and an AND gate 74. The EX.OR gate 72 receives each reference pattern signal generated by the reference pattern memory 52 one by one and each inspecting pattern signal supplied with the terminal "b" of the input selector 48 one by one, and generates an output signal of it. The AND gate 74 receives the output signal of the EX.OR gate 72 and the first domain signal generated by the domain data memory 58, and then delivers a first judging signal to the computer 64.

According to the above procedure, when the first domain signal is "1", the AND gate 74 delivers the first judging signal at a level of "1" to the computer 64 when the inspecting pattern signal does not coincide with the reference pattern signal. The AND gate 74 further delivers the first judging signal as "0" to the computer 64 when the inspecting pattern signal coincides with the reference pattern signal. On the other hand, in a case that the first domain signal is "0", the AND gate 74 always delivers a first masking signal "0" by zeroing the output signal of the EX.OR gate 72.

Figure 4A:
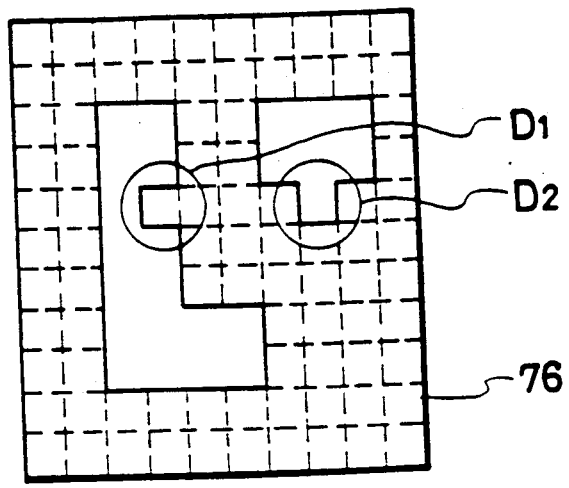
FIGS. 4A, 4B and 4C show examples of an object to be inspected, a reference object and a masking pattern according to the pattern matching method.
Figure 4B:
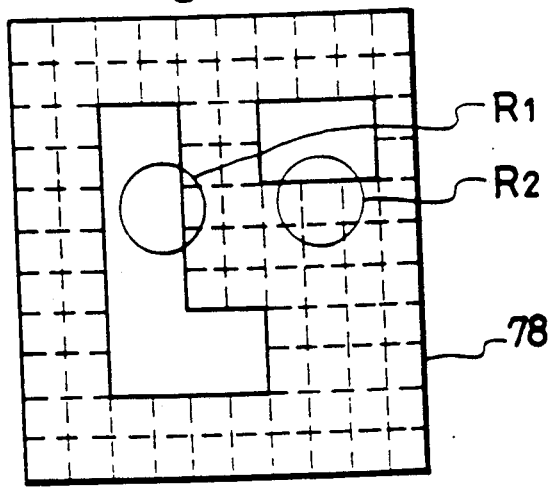
Figure 4C:
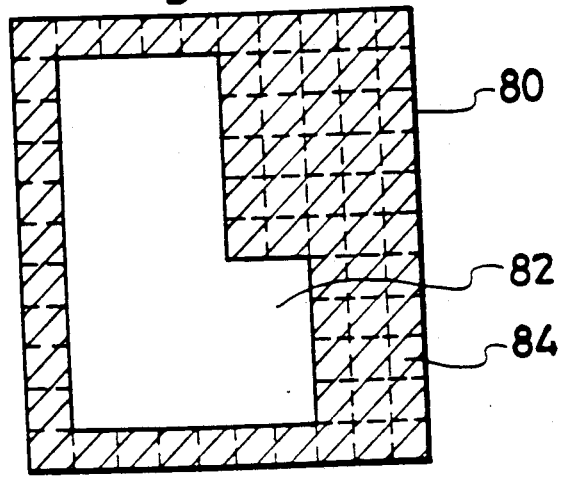

For example, FIG. 4A shows an object 76 to be inspected having two defects of D1 and D2, FIG. 4B shows a reference object 78, and FIG. 4C shows a masking pattern 80 having an inspection domain 82 indicated by "1" and an inhibition domain 84 indicated by "0". The EX.OR gate 72 generates the output signal as "1" when the inspecting pattern signal of the defect D1 is compared with the reference pattern signal of the reference position R1 which corresponds to the defect D1. The AND gate 74 then delivers the first judging signal as "1" to the computer 64, this is because the defect D1 is included in the inspection domain 82, and the AND gate 74 receives the first domain signal in a state "1" at that time.

On the other hand, although the EX.OR gate 72 generates the output signal as "1", the AND gate 74 delivers the first masking signal as "0" to the computer 64 when the inspecting pattern signal of the defect D2 is compared with the reference pattern signal of the reference position R2 corresponding to the defect D2. This is because the defect D2 is included in the inhibition domain 84, and the AND gate 74 receives the first domain signal as "0" at that time.

Figure 5:
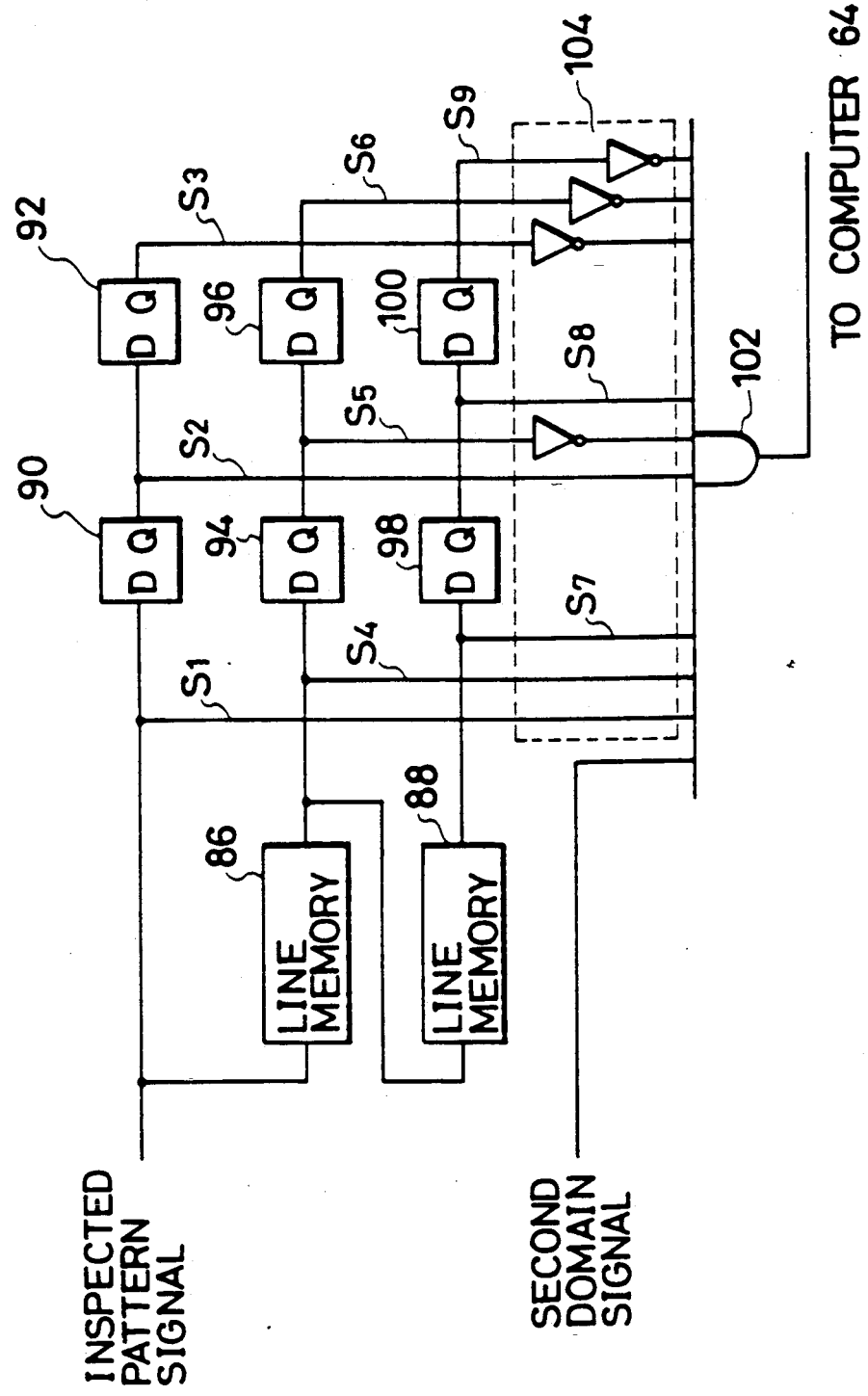
FIG. 5 is a circuit diagram for detecting pattern defects according to the design rule check method.

Referring to FIG. 5, a detailed circuit of the DRCIU 56 for inspecting defects based on the design rule check method shows two line memories 86 and 88 which delay a signal in one scanning line, six delay devices 90-100 which delay a signal in one pixel and which comprise a device such as a D-type Flip-Flop, an AND gate 102 and a decoder 104.

The inspecting pattern signal outputted from the terminal "b" is supplied to the line memory 86, and the line memory 86 supplies a one-line delay signal to the line memory 88 which generates a two-lines delay signal. Each of the inspecting pattern signal delayed in one or two lines is respectively delivered through two cascaded delay devices 90 and 92, 94 and 96, 98 and 100 in order to form a matrix (3×3) of signals S1-S9.

These signals S1-S9 are then supplied by the AND gate 102 through the decoder 104 which includes several inverters and constitutes a circuit for detecting a pattern. The decoder 104, for example, forms a pattern shown in FIG. 6A, and in a case of detecting a pattern shown in FIG. 6B, inverters are inserted in the signals S4, S6, S7, S8 and S9.

The AND gate 102 further receives the second domain signal generated by the domain data memory 60, and then delivers a second judging signal to the computer 64.

Figures 6A, 6B:
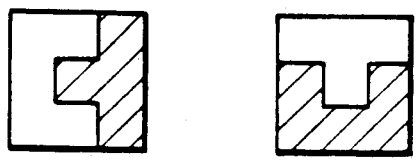
FIGS. 6A and 6B show patterns to be detected according to the design rule check method.

Accordingly, the decoder 104 generates signals which are at "1" when the matrix, which is formed by receiving the inspecting pattern signal one by one, coincides with the pattern to be detected shown in FIGS. 6A and 6B. In a case that the second domain signal is "1", the AND gate 102 delivers the second judging signal as "1" to the computer 64 when every signal generated by the decoder 104 is "1". Further, the AND gate 102 delivers the second judging signal as "0" to the computer 64 when one of the signals generated by the decoder 104 is "0". On the other hand, in a case where the second domain signal is "0", the AND gate 102 always delivers a second masking signal as "0" by masking the output signals of the decoder 104.

Figure 7:
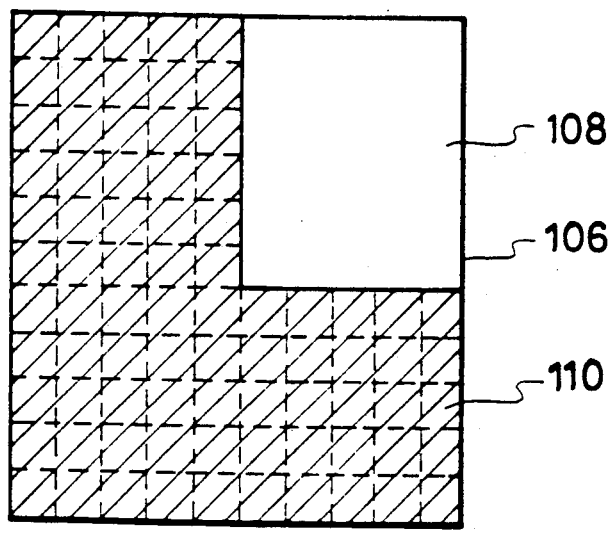
FIG. 7 shows an example of a masking pattern according to the design rule check method.

For example, FIG. 7 shows a masking pattern 106 having an inspection domain 108 indicated by "1" and an inhibition domain 110 indicated by "0". In case of the inspection of the object 76 shown in FIG. 4A, since the defect D1 and the defect D2 coincide with the pattern of FIGS. 6A and 6B, respectively, every signal generated by decoder 104 is "1" when the signals S1-S9 are formed by the inspecting pattern signals of the defect D1 and the boundary thereof, and of the defect D2 and the boundary thereof. The AND gate 102 then delivers the second judging signal as "1" to the computer 64 upon detecting the defect D2 because the defect D2 is included in the inspection domain 108 where the second domain signal is "1". However, the AND gate 102 delivers the second masking signal as "0" to the computer 64 upon detecting the defect D1. This is because the defect D1 is included in the inhibition domain 110 where the second domain signal is "0" at that time.

With the structure of the embodiment as described above, the inspection procedure and its operation are explained as follows.

Referring to FIGS. 8A and 8B, they show a flow chart of the inspection process of the present invention. First of all, the PMIU 54 and the DRCIU 56 are prepared by the user in the inspecting apparatus at a step ST1. The step ST1 includes selecting at least two inspection units which are suitable and preferred for inspecting the object 30 from inspection units having proper inspecting principle respectively, and setting the inspection unit in the apparatus.

In a case where fixed inspection units are not available and being able to exchange them in the apparatus is not possible, the user selects and provides the preferable inspection units in the apparatus. On the other hand, in a case where some inspection units are available in the apparatus in advance, the user only selects the preferable inspection units in the apparatus by switching each inspection unit. The step ST1 serves to initialize the apparatus.

After performing step ST1, first and second domains are defined by the user on defining films at a step ST2. In this embodiment, the first domain is defined by forming the masking pattern 80 (shown in FIG. 4C) on a first defining film by painting the inspection domain 82 or the inhibition domain 84. The second domain is also defined by forming the masking pattern 106 (shown in FIG. 7) on a second defining film by painting the inspection domain 108 or the inhibition domain 110. An inspection domain signifies a domain that is preferred to be inspected, and an inhibition domain signifies a domain which is not for inspecting.

According to the first and second domains defined in step ST2, first and second domain signals are stored in the domain data memories 58 and 60 at step ST3.

On storing the first domain signal, the function of the user is to provide the first defining film on the XY table 28, and to contact the switching lever 50 of the input selector 48 with the terminal "c". In response, the computer 64 enables the domain data memory 58 to write the first domain signals by supplying a write enable signal to the domain data memory 58. According to a reading of an image of the first defining film by scanning it, the domain data memory 58 then starts to write the first domain signals upon receiving each first domain signal delivered with the terminal "c" and the address signal generated by the address controller 62.

On storing the second domain signal, the user provides the second defining film on the XY table 28, and contacts the switching lever 50 with the terminal "d". In response, the computer 64 enables the domain data memory 60 to write the second domain signals by supplying a write enable signal to the domain data memory 60. According to a scanned reading of an image of the second defining film, the domain data memory 60 then starts to write the second domain signals upon receiving each second domain signal delivered with the terminal "d" and the address signal generated by the address controller 62.

Furthermore, it is needed to store the reference pattern signals of the reference object in the reference pattern memory 52 in order to compare the inspecting pattern signal with the reference pattern signal in the PMIU 54. Accordingly, the user also has to provide the reference object on the XY table 28, and to contact the switching lever 50 with the terminal "a". In response, the computer 64 then enables the reference pattern memory 52 to write the reference pattern signals by supplying a write enable signal to the reference pattern memory 52. According to a scanning of an image of the reference pattern, the reference pattern memory 52 starts to write the reference pattern signals delivered through the terminal "a" and the address signal generated by the address controller 62.

The aforementioned steps are preparatory to inspection which is started at a step ST4. The involvement of the user is to turn the switching lever 50 to the terminal "b". In response, the computer 64 enables the reference pattern memory 52 and the domain data memories 58 and 60 to read each signal stored in them by supplying read enable signals to each of the memories 52, 58 and 60. The user then places the object 30 on the XY table 28.

According to the above mentioned preparation steps, the inspection operation is started with the scanning of the object 30, and the apparatus operates as follows.

First of all, an address signal for the memories 52, 58 and 60 is set in the address controller 62 by converting the scanning position signal generated by the scanning controller 42 at a step ST5. Thus the memories 52, 58 and 60 receive the same address signal corresponding to the scanning position on the XY table 28.

Next, the address signal set in step ST5 is compared with the last address of the XY table 28 at step ST6. If the address signal is larger than the last address, the operation is stopped. Contrarily, if the address signal is smaller than or equal to the last address, the operation advances to steps ST7 and ST12.

At steps ST7 and ST12, the inspecting pattern signal is supplied with the PMIU 54 and the DRCIU 56 through the terminal "b" by reading and binarizing the image on the object 30. Then the PMIU 54 and the DRCIU 56 execute their inspection operations. Namely, the PMIU 54 receives the inspecting pattern signal and the reference pattern signal, which are at the same scanning position on the XY table 28, and compares them to each other. As for the DRCIU 56, it receives the inspecting pattern signal only, and judges whether or not the matrix of the signals S1-S9 forms the prescribed pattern as mentioned before.

After the domain data memory 58 has read out the first domain signal in response to receiving the address signal, it delivers it to the PMIU 54 at step ST8. The domain data memory 60 similarly reads out the second domain signal in response to receiving the address signal, and delivers it to the DRCIU 56 at step ST13. Now, the first and second domain signals correspond to the inspecting pattern signal on the point of the scanning position.

At steps ST9 and ST14, the PMIU 54 and the DRCIU 56 judge whether the inspection operations are to be performed at those positions. At step ST9, the operation will advance to step ST10 if the first domain signal is "1", and to step ST11 if the first domain signal is "0". At step ST14, the operation similarly advances to step ST15 if the second domain signal is "1", and to step ST16 if the second domain signal is "0".

The PMIU 54 then delivers the first judging signal as "1" or "0" to the computer 64 at step ST10, and the first masking signal as "0" to the computer 64 at step ST11. Moreover, the DRCIU 56 delivers the second judging signal as "1" or "0" to the computer 64 at step ST15, and the second masking signal as "0" to the computer 64 at step ST16. If, for example, the computer 64 receives the first judging signals as "1", it directs the display unit 66 to display a mark showing the existence of a defect, the address of the defect, and the kind of inspection unit which has detected the defect. Contrarily, the computer 64 directs the display unit 66 to do nothing if it receives the first judging signal as "0" or the first masking signal. The computer 64, of course, operates similarly in a case of receiving the second judging signal and the second masking signal.

Figure 9A:
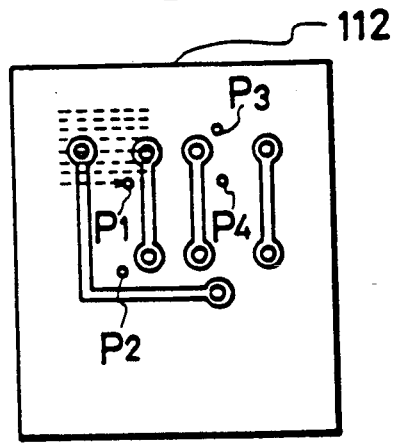
FIGS. 9A, 9B and 9C are explanatory views showing the operation of the pattern defect inspection procedure according to the present invention.
Figure 9B:
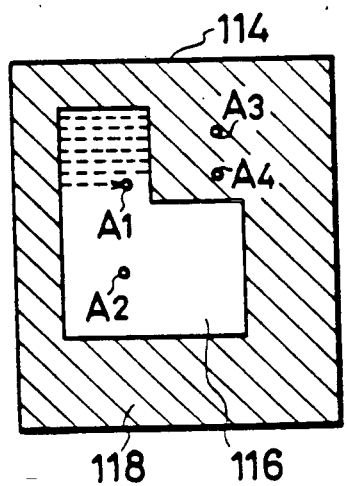
Figure 9C:
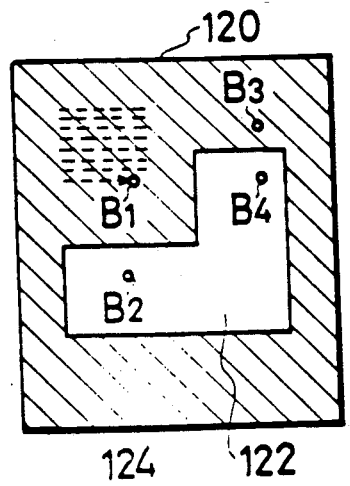

Referring to FIGS. 9A, 9B and 9C, for example, they show an object 112 to be inspected, a first defining film 114 having an inspection domain 116 and an inhibition domain 118, and a second defining film having an inspection domain 122 and an inhibition domain 124. The domain data memory 58 stores a group of first domain signals of the first defining film 114 and the domain data memory 60 stores a group of second domain signals of the second defining film by scanning the defining films 114 and 120.

When a scanning position is located at a position P1 on the object 112, the domain data memory 58 reads out a first domain signal on a position A1 and the domain data memory 60 reads out a second domain signal on a position B1. Thus, step ST10 is performed after performing step ST9 because the first domain signal is "1", and step ST16 is performed after performing step ST14 because the second domain signal is "0". As for a scanning position P2 on the object 112, step ST10 is performed after performing step ST9 and step ST15 is performed after performing step ST14 because the first and second domain signals of value "1" are read out from the domain data memories 58 and 60. As for a scanning position P3 on the object 112, steps ST11 and ST16 are respectively performed after performing steps ST9 and ST14 because first and second domain signals of value "0" are read out from the domain data memories 58 and 60. Moreover, as for a scanning position P4 on the object 112, step ST11 is performed after performing step ST15 because the first domain signal is "0", and step ST12 is performed after performing step ST14 because the second domain signal is "1".

The operation then returns to step ST5 after performing two of steps ST10, ST11, ST15 and ST16 at a step ST17.

Returning to step ST5, a new address signal is set in the address controller 62 by converting the next scanning position signal generated by the scanning controller 42, and the new address signal supplied with each of the memories 52, 58 and 60 as mentioned above. The inspection operation is then performed by repeating steps ST5 to ST17. Moreover, the new address signal is compared with the last address at step ST6, and then the operation stops completely if the new address signal is larger than the last one.

Moreover, as for storing the first domain signals in the domain data memory 58 for instance, it is possible to use CAD data which forms the pattern of the first defining film 114. The CAD data are generally stored in a magnetic tape 68 (shown in FIG. 1). The CAD data are then loaded in the domain data memory 58 from the magnetic tape through the computer 64. In this case, the computer 64 converts the CAD data into the binary signals which comprise the first domain signals. Furthermore, the first domain signal can also be stored in the domain data memory 58 by supplying signals with a digitizer 70 (shown in FIG. 1) through the computer 64. In this case, the computer 64 also converts the digitized signals into the binary signals which form the first domain signals. The reference pattern signal and the second domain signal can naturally be stored in the corresponding memories 52 and 60 in the same manner.

The inspecting apparatus will increase its detecting ability for the defects without difficulty by supplementing it with one or more other inspecting units. Namely, in the invention, it is possible to add another inspecting unit having its own detecting accuracy and ability in the apparatus, also to perform the inspection not only by combination of the PMIU 54 and the DRCIU 56 but also by combination of the other inspecting unit preferable to an object to be inspected.

Figure 10:
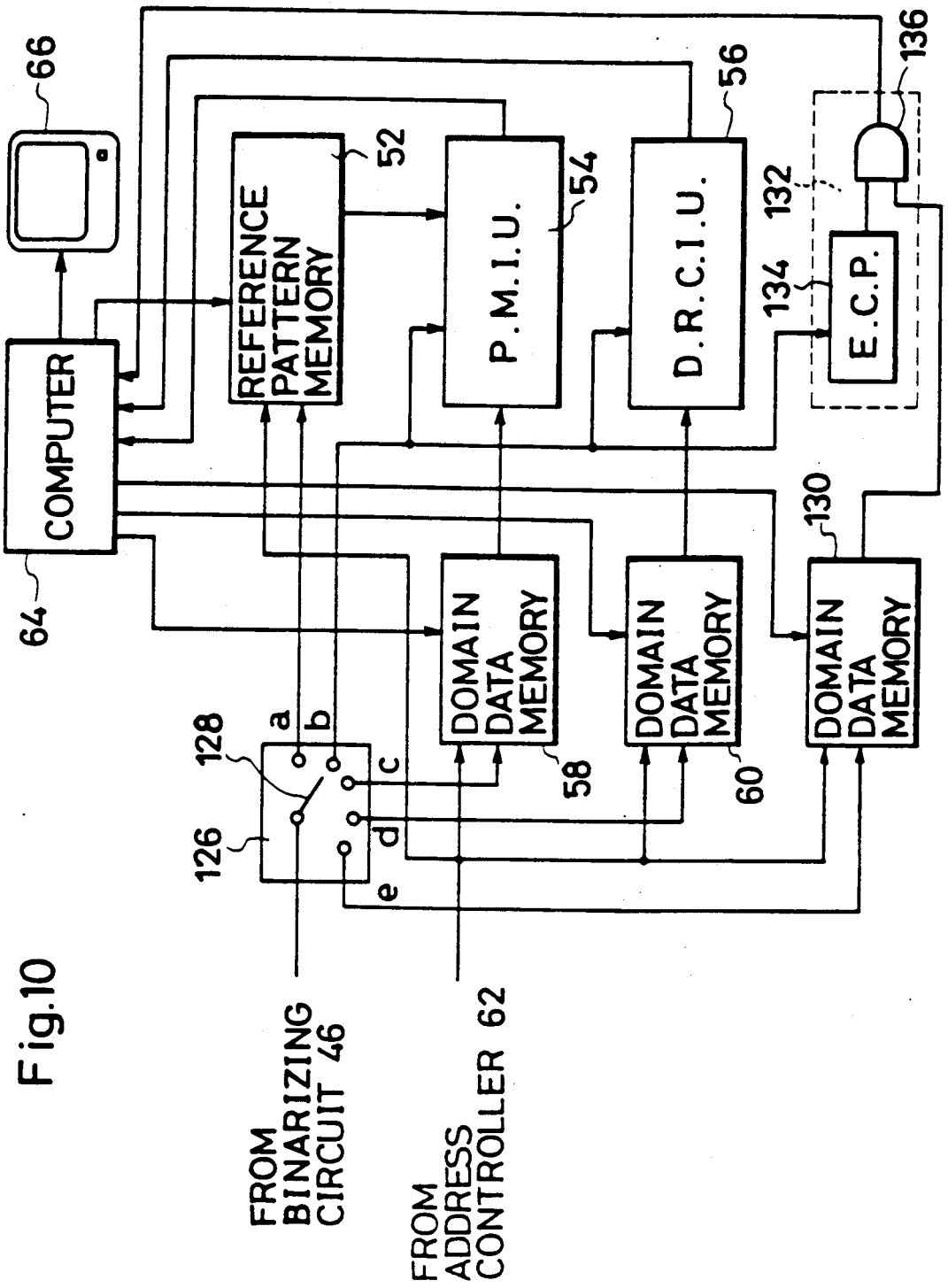
FIG. 10 is a block diagram of a second embodiment of the present invention.

FIG. 10 shows a significant part of a block diagram of a second embodiment. The difference between the first embodiment and this one is mainly in an input selector 126, a domain data memory 130 and an expansion/contraction inspecting unit (hereinafter referred to as "ECIU") 126. In the second embodiment, steps or elements described in the first embodiment are referred to by the same reference numbers.

The input selector 126 has a switching lever 128 and comprises terminals "a", "b", "c", "d" and "e". The input selector 126 receives the binary signal generated by the binarizing circuit 46 (shown in FIG. 1), and delivers it to one of the terminals through the switching lever 128. The connection of the terminals correspondingly applies to the first embodiment. Namely, their connections are as follows: the terminal "a" is connected to the reference pattern memory 52; the terminal "b" to the PMIU 54, the DRCIU 56 and to the ECP 134, the terminal "c" to the domain data memory 58, the terminal "d" to the domain data memory 60, and the terminal "e" to the domain data memory 130.

The domain data memory 130 receives the address signal generated by the address controller 62 (specified in the first embodiment), a write enable signal and a read enable signal supplied with the computer 64. The domain data memory 130 then stores a group of third domain signals, which define, for example, the read and binarized representation of an image of a masking pattern 138 shown in FIG. 11, for controlling the inspection operation in the ECIU 132.

The ECIU 132 comprises an expansion/contraction process (hereinafter referred to as "ECP") 134 and an AND gate 136. The ECP 134 is provided to detect fine defects based on an expansion/contraction method, and receives the inspecting pattern signal delivered at the terminal "b". The AND gate 136 receives a third judging signal generated by the ECP 134 and a third domain signal generated by the domain data memory 130, and supplies the third judging signal when the third domain signal is "1" and a masking signal when the third domain signal is "0" to the computer 64.

FIG. 12 is helpful for explaining the principle behind the expansion/contraction process. An illustration (a) shows an object to be inspected comprising a white pattern WP and a black pattern BP, which have a first fine defect DT1 and a second fine defect DT2 associated therewith. An illustration (b) is obtained by expanding the black pattern BP of the illustration (a). An illustration (c) is then obtained by subsequently recontracting the black pattern BP of the illustration (b), and shows the same pattern as the illustration (a) unless having disappeared the first fine defect DT1. This is because the first fine defect DT1 cannot be restored to its original state since it has already disappeared in the illustration (b). Therefore, the first fine defect DT1 of an illustration (d) is detected by comparing the pattern of the illustration (a) and the pattern of the illustration (c).

On the other hand, an illustration (e) is obtained by contracting the black pattern BP of the illustration (a). An illustration (f) is then obtained by expanding the black pattern BP of the illustration (e), and shows the same pattern as the illustration (a) unless the second fine defect DT2 had disappeared. This is because the second fine defect DT2 cannot be restored to its original state since it has already disappeared in the illustration (e). Therefore, the second fine defect DT2 of an illustration (g) is detected by comparing the pattern of the illustration (a) and the pattern of the illustration (f).

The ECP 134 then detects fine defects based on such processing, and supplies the third judging signal to the AND gate 136.

The same inspection and operation procedures are correspondingly applied to the first embodiment. Referring to FIGS. 8A and 8B again, at steps ST1–ST3, step elements concerned with the ECP 134 are incorporated in each step ST1, ST2 and ST3. Namely, the first of them is to prepare the ECP 134 at step ST1, and the second is to define the third domain on a third defining film by forming the third masking pattern 138 for example at step ST2, and further the third is to store the third domain signal in the domain data memory 130.

On storing the third domain signal at step ST3, the user's involvement is to provide the third defining film on the XY table 28, and to place the switching lever 128 of the input selector 126 to contact the terminal "e". In response, the computer 64 enables the domain data memory 130 to write the third domain signal by supplying a write enable signal to the domain data memory 130. According to the reading of an image of the third defining film by a scanning process, the domain data memory 130 then starts to write the third domain signal in response to receiving the third domain signal delivered from the terminal "e" and the address signal generated by the address controller 62.

The inspection operation is then started at step ST4 according to the above mentioned description, and steps ST5 and ST6 are the same as those of the first embodiment in the operations.

Figure 13:
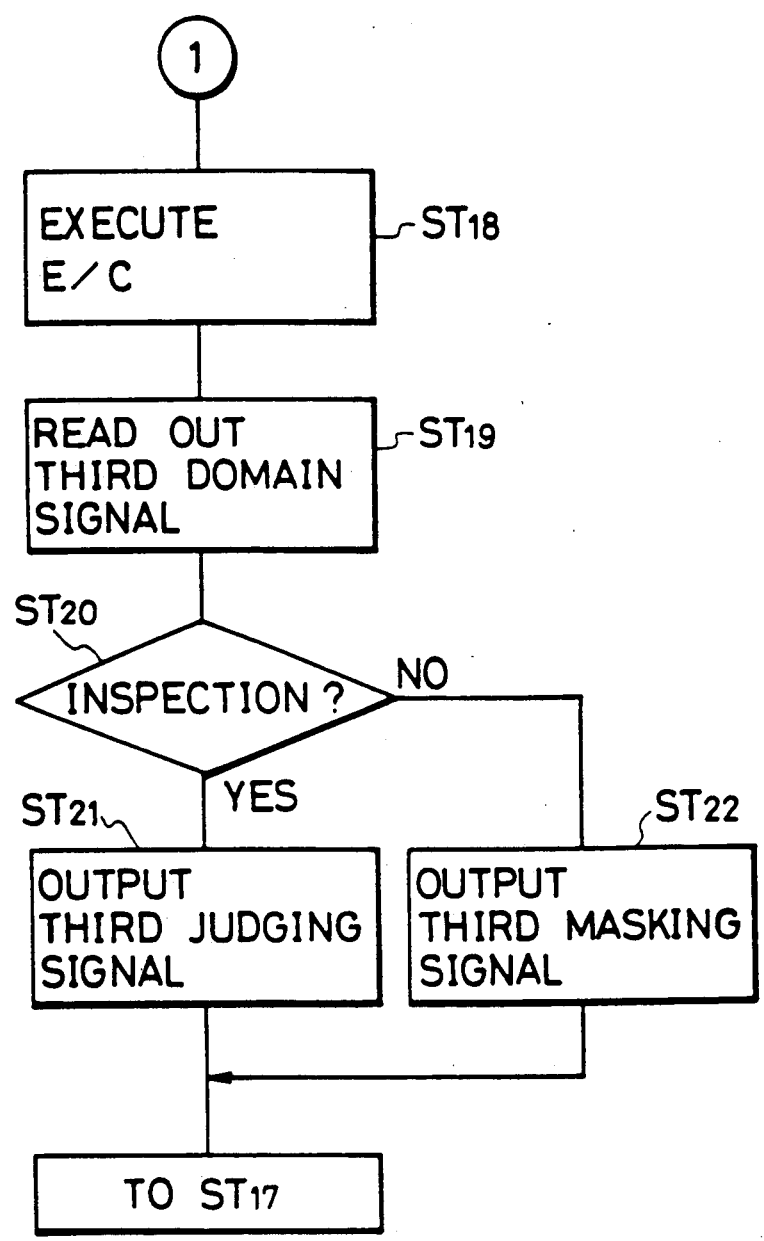
FIG. 13 is a part of a flow chart showing steps of a pattern defect inspection process in accordance with the second embodiment.

Upon performing step ST6, steps ST18–ST22 are simultaneously performed with steps ST7–ST11 and steps ST12–ST16. The steps ST18–ST22 are shown in FIG. 13. They are the same as steps ST7–ST11 and/or steps ST12–ST16 in the operation which they designate. Namely, at steps ST18, the inspecting pattern signals are supplied to the ECIU 132 through the terminal "b" by reading and binarizing the image of the object 30. Then the ECIU 132 executes its inspection operation. The ECP 134 receives the inspecting pattern signal only, and judges whether or not those signals include the defects, by carrying out the expansion/contraction processing as mentioned above.

The domain data memory 130 reads out the third domain signal in response to receiving the address signal, and delivers it to the AND gate 136 in the ECIU 132 at step ST19. Now, the third domain signal also corresponds to the inspecting pattern signal on the point of scanning position.

At step ST20, the ECIU 132 judges whether the inspection operation has been performed at that position, and the operation advances to step ST21 when the third domain signal is "1" and to step ST22 when the third domain signal is "0".

The ECIU 132 then delivers the third judging signal as "1" or "0" to the computer 64 at step ST21, and the third masking signal, which is "0", to the computer 64 at step ST22. If the computer 64, for example, receives the third judging signals as a "1", it directs the display unit 66 to display a mark showing existence of a defect, the address of the defect, and the kind of inspection unit which has detected the defect.

Upon performing three of the steps ST10, ST11, ST15, ST16, ST21 and ST22, the operation returns to step ST5 through step ST17. Returning to step ST5, the inspection operation is then performed by repeating the steps from ST5 to ST22. Moreover, a new address signal is compared with the last address at step ST6, and then the operation stops completely if the new address signal is larger than the last one.

Figure 14:
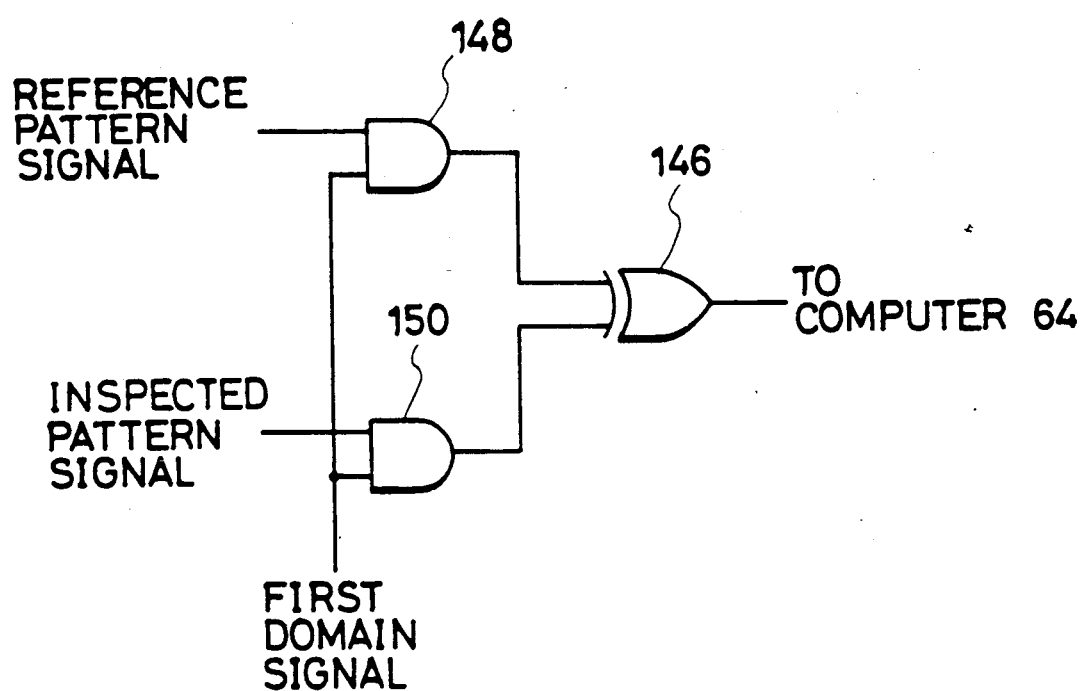
FIG. 14 is another circuit diagram detecting pattern defects according to the pattern matching method.
Figure 15:
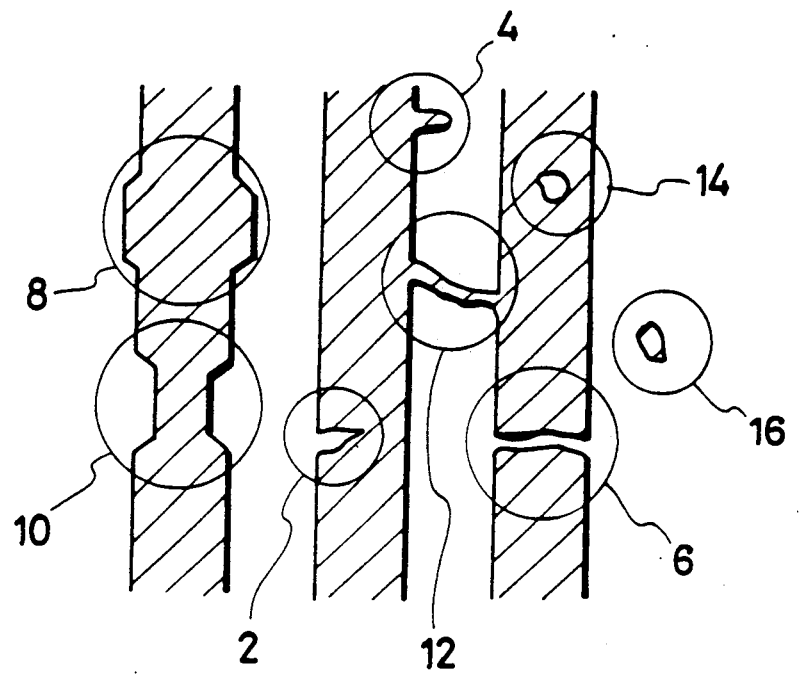
FIG. 15 shows examples of pattern defects.
Figure 16:
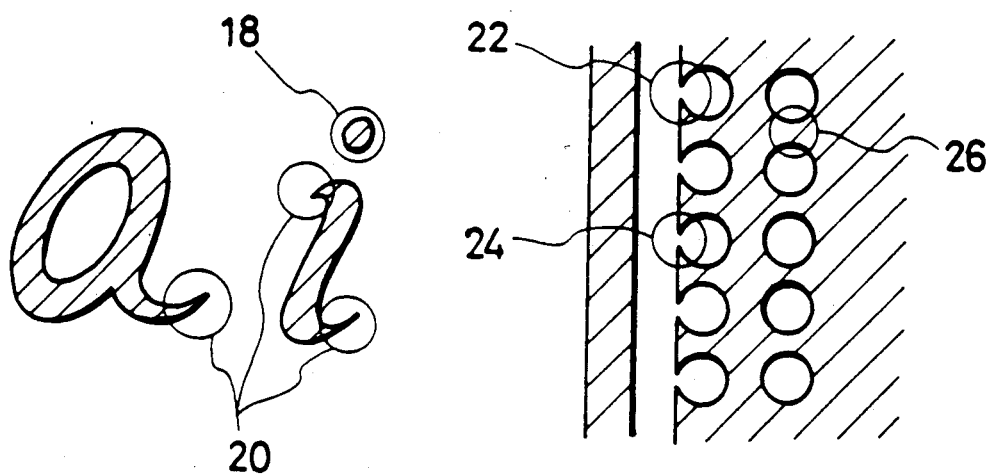
FIG. 16 is an explanatory view showing examples of detecting errors according to the design rule check method.

This invention can be practiced or embodied in other ways. For example, while in the illustrated preferred embodiments, the AND gate 74, for instance, controls whether or not the PMIU 54 performs the inspection operation according to the first domain signal. This function can be done by another structure, shown in FIG. 14. An EX.OR gate 146 receives the reference pattern signal through an AND gate 148 and the inspecting pattern signal through an AND gate 150. The AND gates 148 and 150 further receive the first domain signal respectively, and the EX.OR gate 146 supplies an output signal thereof to the computer 64. According to this structure, the EX.OR gate 146 supplies the first judging signal when the first domain signal is "1", and the first masking signal when the first domain signal is "0" to the computer 64. This is because, when the first domain signal is "0" the EX.OR gate 146 always receives two input signals of "0", and it therefore generates an output of "0". It means that it is practicable to control the inspection operation by nullifying input signals of inspecting units instead of nullifying judging signals thereof.

Although the domain signals are stored in the domain data memories 58 and 60 by scanning the defining films 114 and 120, the same function can be done by scanning defining plates having at least one hole forming an inspection domain or an inhibition domain by punching them with a press and so on. A paper forming an inspection domain and an inhibition domain which are divided on the basis of a difference of color, density and the like is also applicable to this matter.

The present invention may be embodied in other specific forms without departing from the spirit or essential attributes thereof and, accordingly, the appended claims, rather than to the foregoing specification, are indicative of the scope of the present invention.

What is claimed is:

1. A method of inspecting an object to detect pattern defects thereof, comprising the steps of:
   (a) providing a plurality of inspecting units each of which operates in accordance with a respective inspecting principle;
   (b) defining, in a defining means, an inspection domain which forms a source of the inspection signals and an inhibition domain which forms a source of the inhibition signals, said inspection and inhibition domains being defined for each inspecting unit on the object;
   (c) obtaining groups of domain signals on the basis of each image of the defining means, each said group of domain signals comprising inspection signals and inhibition signals;
   (d) storing groups of domain signals in a memory in addresses thereof which correspond to positions on the object, each said group of domain signals having a particular relation to a respective one of the inspecting units;
   (e) binarizing an image of the object;
   (f) reading out the domain signals of every group of the domain signals from the memory according to inspection position addresses on the object;
   (g) controlling the operation of each inspecting unit according to the type of domain signals read out therefor from the memory; and
   (h) forming an inspection decision according to an output signal of the inspecting units.

2. A method in accordance with claim 1, wherein said groups of domain signals are obtained by scanning and binarizing each image of the defining means.

3. A method in accordance with claim 2, wherein the defining means is a film on which at least one of the inspection domain is formed and the inhibition domain.

4. A method in accordance with claim 2, wherein the defining means is a plate with a punched hole which forms either the inspection domain or the inhibition domain.

5. A method in accordance with claim 1, wherein the groups of domain signals are stored in the memory by receiving groups of binary signals, each said group of binary signals comprising an inspection domain and an inhibition domain.

6. A method in accordance with claim 5, wherein the group of the binary signals is obtained by converting CAD data created with a CAD system into the binary signals.

7. A method in accordance with claim 5, wherein the group of the binary signals is obtained by converting digitized signals generated with a digitizer into the binary signals.

8. A method in accordance with claim 1, wherein the operation of the inspecting unit is inhibited when the inhibition signal of the inspecting unit is read out from the memory.

9. A method in accordance with claim 8, wherein an output signal of the inspecting unit is nullified by a gate means according to the state of an inhibition signal read out from the memory.

10. A method in accordance with claim 8, wherein an input signal of the inspecting unit is nullified by a gate means according to the state of an inhibition signal read out from the memory.

11. An apparatus for inspecting and finding pattern defects of an object to be inspected, comprising:
   image signal generating means for generating image signals of the object;
   a plurality of inspecting units for inspecting and finding pattern defects, if any, on the object by using the image signals of the object, each said inspecting unit operating in accordance with a respective inspecting principle;
   domain signal generating means for generating domain signals expressing an image pattern defined on the object, said image pattern having an inspection domain and an inhibition domain;
   a memory for storing groups of the domain signals, each said group of domain signals having a particular relation to a respective one of the inspecting units;
   an access controller for controlling reading and writing of the domain signals in the memory according to positions of the image pattern;
   an inspection controller for controlling the operation of each inspecting unit in response to the respective domain signals read out from the memory; and
   forming means for forming an inspection decision in response to output signals of the inspecting units.

12. An apparatus in accordance with claim 11, wherein the domain signal generating means comprises a CAD system which creates CAD data forming an inspection domain and an inhibition domain, and converting means for converting the CAD data into the domain signals.

13. An apparatus in accordance with claim 11, wherein the domain signal generating means comprises a digitizer which generates digitized signals forming an inspection domain and an inhibition domain, and converting means for converting the digitized signals into the domain signals.

14. An apparatus in accordance with claim 11, wherein the inspection controller is effective for inhibiting the operation of the inspecting unit in response to the inhibition signal read out from the memory.

15. An apparatus in accordance with claim 14, further comprising gate means and wherein operation of the inspecting unit is inhibited by nullifying an output signal of the inspecting unit with the gate means.

16. An apparatus in accordance with the claim 14, further comprising gate means and wherein the operation of the inspecting unit is inhibited by nullifying an input signal of the inspecting unit with the gate means.

17. The method of claim 1, further comprising displaying an indication whenever a defect has been located.

18. A method in accordance with claim 17, further comprising displaying additionally the location of the defect and the type of inspecting unit which has detected it.

19. A method in accordance with claim 1, wherein said binarizing of an image is carried out by scanning the image of the object.

* * * * *